(12) United States Patent
Yoshinari et al.

(10) Patent No.: US 6,503,918 B2
(45) Date of Patent: *Jan. 7, 2003

(54) D-MANNITOL AND ITS PREPARATION

(75) Inventors: Tomohiro Yoshinari, Suita (JP); Fritz Schueckler, Leverkusen (DE); Norbert Poellinger, Muellheim (DE); Shinji Maegata, Koka-gun (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/029,834

(22) Filed: Dec. 31, 2001

(65) Prior Publication Data

US 2002/0107420 A1 Aug. 8, 2002

Related U.S. Application Data

(60) Continuation of application No. 09/650,722, filed on Aug. 30, 2000, now abandoned, which is a division of application No. 09/155,978, filed on Oct. 23, 1998, now Pat. No. 6,235,947.

(30) Foreign Application Priority Data

Apr. 16, 1996 (JP) .............................................. 8-094401

(51) Int. Cl.$^7$ ............................................. A61K 31/435
(52) U.S. Cl. ....................................... 514/277; 514/960
(58) Field of Search ................................ 514/960, 277; 568/852, 868

(56) References Cited

U.S. PATENT DOCUMENTS

| | | | |
|---|---|---|---|
| 3,145,146 A | 8/1964 | Lieberman et al. | 167/82 |
| 4,507,511 A | 3/1985 | Reiff et al. | 568/852 |
| 4,661,647 A | 4/1987 | Serpelloni et al. | 568/868 |
| 4,803,213 A | 2/1989 | Iida et al. | 514/355 |
| 5,006,530 A | 4/1991 | Angerbauer et al. | 514/277 |
| 5,064,829 A | 11/1991 | Izuhara et al. | 514/249 |
| 5,160,680 A | 11/1992 | Serpelloni et al. | 264/126 |
| 5,177,080 A | 1/1993 | Angerbauer | 514/277 |
| 5,324,751 A | 6/1994 | DuRoss | 514/777 |
| 5,356,896 A | 10/1994 | Kabadi et al. | 514/256 |
| 5,573,777 A | 11/1996 | Serpelloni et al. | 424/440 |
| 5,817,028 A | 10/1998 | Anderson | 600/529 |
| 6,235,947 B1 * | 5/2001 | Yoshinari | |

FOREIGN PATENT DOCUMENTS

| EP | 0 380 219 A2 | 8/1990 |
|---|---|---|
| EP | 0 645 096 A1 | 3/1995 |

OTHER PUBLICATIONS

Harry G. Brittain, "Overview of Physical Characterization Methodology" Chapter 1, Physical Characterization of Pharmaceutical Solids, pp. 1–35, Marcel Dekker Inc., New York, 1995.
Declaration of Liesbeth Maria Fernande Meeus dated Feb. 4, 2002.
F. T. Jones and K. S. Lee, "The Optical and Crystallographic Properties of Three Phases of Mannitol", Microscope 18, pp. 279–285, 1970.
Anne Mari Juppo, "Porosity parameters of lactose, glucose, and mannitol tablets obtained by mercury porosimetry", International Journal of Pharmaceutics, vol. 129, pp 1–12, Mar. 1996.
Alexandra I. Kim et al., "The Physical State of Mannitol after Freeze–Drying; Effects of Mannitol Concentration, Freezing Rate, and a Noncrystallizing Cosolute", Journal of Pharmaceutical Sciences, vol. 87, pp. 931–935, Aug. 1998.
Henry R. Constantino et al., "Effects of Mannitol Crystallization on the Stability and Aerosol Performance of a Spray–Dried Pharmaceutical Protein, Recombinant Humanized Antigen–IgE Monoclonal Antibody", Journal of Pharmaceutical Sciences, vol. 87, pp. 1406–1411, 1998.
Joseph L. Kanig, "Properties of Fused Mannitol in Compressed Tablets", Journal of Pharmaceutical Sciences, vol. 53, No. 2, pp. 188–192, Feb. 1964.
B. Debord et al., "Study of Different Crystalline Forms of Mannitol: Comparative Behaviour Under Compression", Drug Development and Industrial Pharmacy, 13 (9–11), pp. 1533–1546, (1987).
Remington: "The Science and Practice of Pharmacy", 19$^{th}$ Ed. pp. 1615–1641, (1995).

* cited by examiner

Primary Examiner—Michael L. Shippen
(74) Attorney, Agent, or Firm—Wenderoth, Lind & Ponack, L.L.P.

(57) ABSTRACT

D-mannitol having a specific surface area of not less than about 1 m$^2$/g is disclosed. The D-mannitol shows improved compressibility and is useful as an excipient.

3 Claims, 5 Drawing Sheets

D-MANNITOL AND ITS PREPARATION

This application is a Continuation Application of U.S. patent application Ser. No. 09/650,722, filed Aug. 30, 2000, now abandoned, which is a Divisional Application of U.S. patent application Ser. No. 09/155,978, filed Oct. 23, 1998, now U.S. Pat. No. 6,235,947, issued May 22, 2001.

BACKGROUND OF THE INVENTION

1. Field of the Invention

The present invention relates to a novel D-mannitol and its preparation. More specifically, it relates to D-mannitol which can be used as an excipient with excellent compressibility in the fields of preparation of medicaments and food processing industry, and a process for preparing it.

2. Description of the Related Art

D-mannitol is excellent in safety and in its compatibility with physiologically active substances. And, since it is not hygroscopic and retains no substantial moisture, it is of high value as an excipient for formulation of, especially, a physiologically active substance of high moisture sensitivity into tablets or capsules. On the other hand, D-mannitol is poor in bindability when subjected to compression and, besides, its friction with a metal wall is strong. These shortcomings tend to cause die friction or capping upon compression, which fails to give sufficient hardness to the aimed tablets, giving wear on the wall of a die and on the side face of a punch, even making sometimes the running of a tabletting machine difficult. In view of the foregoing, use of D-mannitol as excipient has been restricted in very limited dosage forms such as chewable tablets.

D-mannitol is a crystalline powder having polymorphic forms classified into α form, β form and δ form by X-ray diffraction patterns [Walter-Levy, L., Acad. Sc. Paris, t. 267 Series C, 1779 (1968)]. For improving the compressibility of crystalline powder, it has been known that, in general, crystals are finely ground to increase the binding points to give a better compressibility. However, in the case of D-mannitol, mere grounding of it into fine powder enhances the friction with the metal wall when subjected to compression, and also involves problems on its handling such as dusting and lowering of fluidity.

And, in Journal of Pharmaceutical Sciences, 53 (2), 188–192 (1964), there is a report on a method of obtaining D-mannitol improved in its compressibility, which comprises fusing D-mannitol and, immediately cooling. However, the improvement in compressibility brought by this method is not the one sufficiently meeting the requirements in the formulation process. Besides, the procedure is specific, so that it is difficult to apply to a industrial production scale, leaving a problem from the viewpoint of cost.

One object of the present invention is to provide D-mannitol by a simple procedure, which is excellent in powder properties and dramatically improved in compressibility.

Another object of the present invention is to provide a process for preparing D-mannitol.

Still another object of the present invention is to provide a solid composition comprising D-mannitol as an excipient.

These objects as well as other objects and advantages of the present invention will be apparent to those skilled in the art from the following description with reference to the accompanying drawings.

Under these circumstances, the present inventors have studied intensively to establish a process for preparing D-mannitol excellent in powder properties and improved in compressibility, by a simple procedure. As a result, it has been found that, when δ form crystals are brought into contact with a water-soluble solvent, they are transformed into β form at the contact interface to give fine crystalline precipitates. This phenomenon has suggested to the present inventors that D-mannitol composed of an aggregation of fine crystals could be obtained. The present invention has been completed by the present inventor's further intensive investigation based on this suggestion.

SUMMARY OF THE INVENTION

That is, according to the present invention, there is provided D-mannitol having a specific surface area of not less than about 1 $m^2/g$, in particular, such D-mannitol comprising a mixture of δ form crystals and β form crystals.

In another aspect, the present invention provides a process for preparing D-mannitol having a specific surface area of not less than about 1 $m^2/g$ which comprises treating δ form D-mannitol crystals with a water-soluble solvent, followed by drying. In this aspect, it is preferred to use the water-soluble solvent in an amount of about 3 to about 70 W/W% based on the weight of the δ form D-mannitol crystals.

In still another aspect, the present invention provides a solid composition comprising D-mannitol having a specific surface area of not less than about 1 $m^2/g$. Preferably, the solid composition of the present invention further comprises a pharmacologically active component, for example, a highly moisture-sensitive component, in particular, sodium 3R, 5S-(+)-erythro-(E)-7-[4-(4-fluorophenyl)-2,6-diisopropyl-5-methoxymethyl-pyrid-3-yl]-3,5-dihydroxy-hept-6-enoate.

BRIEF DESCRIPTION OF THE DRAWINGS

In FIG. 1, the open circle and the open square respectively show the comparative compressed products using untreated δ form crystals and β form crystals, while the closed circle and the closed square respectively show the results observed in the compressed product prepared b using treated crystals of Example 1 and Comparative Example 1.

DESCRIPTION OF THE PREFERRED EMBODIMENTS

Figure 1:
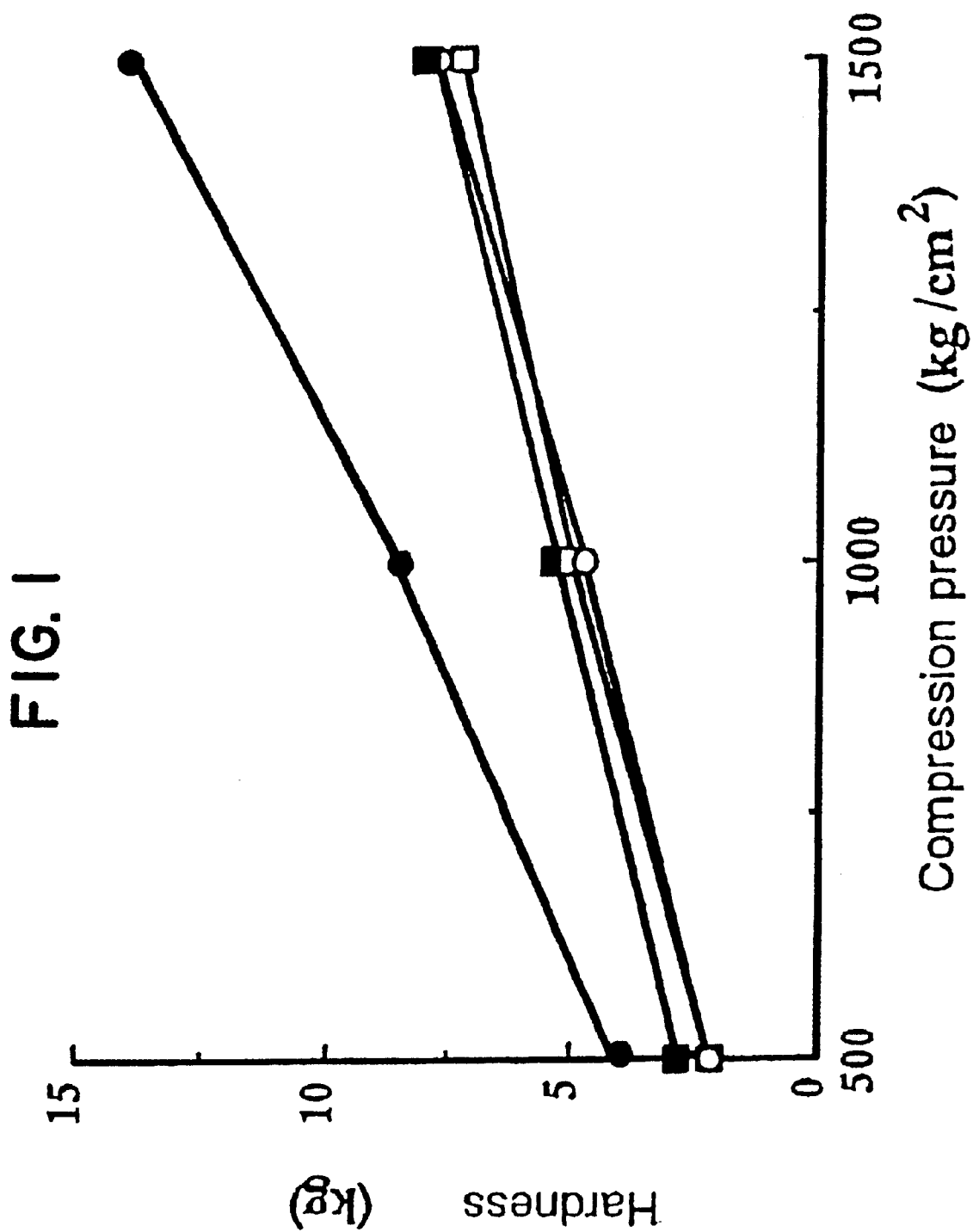
FIG. 1 is a graph illustrating the hardness of the compressed products prepared in Example 1 and that of the compressed product prepared in Comparative Example 1 hereinafter.

The D-mannitol of the present invention is the β form crystals alone or a mixture thereof with the δ form crystals, which is an aggregate of D-mannitol crystals whose specific surface area is not less than about 1 m²/g, preferably not less than about 1.5 m²/g, normaly about 1.5 to about 4 m/g.

The specific surface area used herein is that calculated by the BET method widely used in general.

From the viewpoint of convenience of utilizing as additives or excipients of pharmaceutical preparations or food products, D-mannitol is preferably in the state of granules of crystalline aggregate especially whose average size is about 0.05 to about 5.0 mm, more preferably about 0.08 to about 2.0 mm in diameter. However, forms of the crystalline aggregate is not specifically limited and any form of crystal line aggregate which meet the requirements and, for example, net-like or thin plate-like ones are included in the present invention, in so far as the aggregate has the above-described properties.

The α form, β form and δ form D-mannitol crystals described herein are defined in accordance with the classification of polymorphic forms by X-ray diffraction pattern reported in Acad. Sc. Paris, t. 267 Series C, 1779, (1968) by Walter-Levy, L.

The D-mannitol of the present invention can be prepared by a method which comprises treating the δ form crystals employed as the starting material with a water-soluble solvent and then drying the treated material, preferably, by subjecting it to rapid drying to cause transformation of the surface or inside of the starting crystals into fine β form crystals. More specifically, the method comprises a step of moistening the surface of the δ form crystals with a water-soluble solvent to cause successive transformation of a portion or all of the δ form crystals reacted with the solvent into the β form from the surface to the inside, and a step of drying to suppress the growing of the resultant β form crystals. Then, normally, D-mannitol of the present invention exists as a mixture of δ form crystals and β form crystals. The ratio of δ form crystals and β form crystals in the mixture is defined by the above transformation step of the crystal form and crystal growing step. However, it is not specifically limited.

For treating the δ form crystals with a water-soluble solvent, any means which can moisten the surface of individual crystals without dissolving completely in a water-soluble solvent, for example, spraying a water-soluble solvent on a thin layer of the δ form crystals or agitating while spraying or dropping a water-soluble solvent on the δ form crystals, can be employed. And, in this treatment, other component may optionally be coexisted in so far as the surface of D-mannitol crystals can be moistened. For example, as described in the Examples hereinafter, treatment of a portion or of the whole mixture of a formulated end product containing D-mannitol with a water-soluble solvent also falls within the scope of this invention.

Examples of the water-soluble solvent include purified water, methanol, ethanol, acetone or a mixture thereof, and the mixing ratio is suitably chosen depending on necessity. Among them, purified water, ethanol and a mixture thereof are preferably employed.

The amount of the water-soluble solvent to be used is suitably chosen according to a particular treatment of crystals, a particular solvent to be used or the like, normally, from the range of about 3% to about 70%, preferably about 15% to about 40% by weight based on the weight of the starting crystals. For example, in the case of employing a method comprising addition of the water-soluble solvent to the starting crystals and agitating the mixture, preferably, the water-soluble solvent is added in an amount of about 5 w/w% or more in view of the diffusion rate of the water-soluble solvent. or more in view of the diffusion rate of the water-soluble solvent.

In the drying step, for suppressing the growth of fine crystals developed by the above-described method, the time required for drying is preferably as short as possible. Therefore, normally, rapid drying are preferred in many cases. On the other hand, the starting crystals can continue the transition caused by treatment with the water-soluble solvent until completing the transition to the β form. Then, the drying in the method of the present invention is determined depending on the relation with the transition rate of the crystals, thus the drying time is not specifically limited. Therefore, for example, in the case of the method comprising admixing the starting crystals with purified water, it is preferred to remove purified water within 48 hours, preferably 16 hours, more preferably 8 hours after the crystals and purified water are homogeneously mixed. However, the time can of course be varied with, for example, the treatment method, solvent and drying method employed. Examples of the drying method include vacuum drying, air drying, fluidized bed drying and dielectric high frequency drying and the like, and, among them, vacuum drying is preferred.

The thus-obtained D-mannitol of the present invention has the above-described specific surface area and exhibits an excellent compressibility, which can be used as an excipient for direct compression, wet-granulation or dry-granulation. The mannitol can be used as a good excipient in the fields of pharmaceutical and food products. It is especially useful for the production of a solid composition comprising a pharmacologically active component, a sweetener or the like.

The solid composition of the present invention comprises D-mannitol having a special surface area of not less than about 1 m/g. The composition of the present invention further comprises, preferably, a pharmacologically active component, a sweetener or the like. The composition can contain a pharmacologically active component, a sweetener or the like in an effective amount thereof. In particular, the composition of the present invention preferably comprises a pharmacologically active component.

Examples of the pharmacologically active component include physiologically active peptides, anti-tumor agents, antibiotics, antipyretics, analgesics, anti-inflammatory agents, antitussive expectorants, bronchodilators, sedativa, muscle relaxants, antiepileptics, antiulcer agents, antidepressant agents, antiallergic agents, cardiotonics, antiarrhythmic agents, vasodilators, hypotensive diuretics, antidiabetics, antilipidemic agents, anticoagulants, hemostatics, antituberculous agents, hormones, narcotic antagonists, bone resorption inhibitory agents, osteogenesis promoting agents, angiogenesis inhibitory agents, vitamins and the like.

Examples of the physiologically active peptides include LH-RH (luteinizing hormone releasing hormone) agonists [U.S. Pat. Nos. 3,853,837, 4,008,209 and 3,972,859; British Patent No. 1,423,083; Proceedings of the National Academy of Sciences of the United States of America, 78, 6509–6512 (1981)], LH-RH antagonists (U.S. Pat. Nos. 4,086,219, 4,124,577, 4,253,997, 4317,815 and 5,480,868), insulin, somatostatin, somatostatin derivatives (sandostatin, U.S. Pat. Nos. 4,087,390, 4,093,574, 4,100,117 and 4,253,998), growth hormone, prolactin, adrenocorticotropic hormone (ACTH), ACTH derivatives (e.g., ebiratide, etc.), melanocyte-stimulating hormone (MSH), thyrotropin-releasing hormone (TRH) and its derivatives (JP-A 50-121273 and JP-A 52-116465), thyroid-stimulating hormone (TSH), luteinizing hormone (LH), follicle-stimulating hormone (FSH), vasopressin, vasopressin derivatives [desmopressin (Nippon Naibunpi Gakkaishi, 54, 5, 676–691 (1978))], oxytocin, calcitonin, parathyroid hormone (PTH), gulcagon, gastrin, secretin, pancreozymin, cholecystokinin, angiotensin, human placental lactogen, human chorionic gonadotropin (HCG), enkephalin, enkephalin derivatives (U.S. Pat. No. 4,277,394, EP-A 31567), endorphin, kyotorphin, interf erons (e.g., IFN-α, β, γ, etc.) interleukins (e.g., IL-1, 2, 3, 4, 5, 6, 7, 8, 9, 10, 11, 12, etc.), tuftsin, thymopoietin, thymosin, thymostimulin, thymic humoral factor (THF), blood thymic factor (FTS) and its derivatives (U.S. Pat. No. 4,229,438) and other thymic factors [Igaku no Ayumi, 125, 10, 835–843 (1983)], tumor necrosis factor (TNF), colony stimulating factors (CSF, GCSF, GMCSF, MCSF, etc.), motilin, dynorphin, bombesin, neurotensin, caerulein, bradykinin, urokinase, asparaginase, kallikrein, substance P, insulin-like growth factors (IGF-I, IGF-II), nerve growth factor (NGF), cell growth factors (EGF, TGF-α, TGF-β, PDGF, acidic FGF, basic FGF, etc.), osteogenesis factor (BMP), neurotrophic factors (NT-3, NT-4, CNTF, GDNF, BDNF, etc.), blood coagulation factors VIII and IX, lysozyme chloride, polymyxin B, colistin, gramicidin, bacitracin and erythropoietin (EPO), thrombopoietin (TPO), polypeptides having endothelin antagonistic activity (EP-A 436189, 457195 and 496452; JP-A 3-94692, JP-A 3-130299) and the like.

Examples of anti-tumor agents include Bleomycin, Methotrexate, Actinomycin D, Mytomycin C, Vinblasine sulfate, Vincristine sulfate, Daunorbicin, Adriamycin, Neocarzinostatin, cytosine arabinoside, Fluorouracil, tetrahydrofuryl-5-fluorouracil, Klestin, Picibanil, Lentinan, Levamisole, Bestatin, Azimexon, Glycyrrhizin, poly I:C, poly A:U, polyICLC and the like.

Examples of antibiotics include Gentamicin, Dibekacin, Kanendomycin, Lividomycin, Tobramycin, Amikacin, Fradiomycin, Sisomicin, Tetracycline hydrochloride, Oxytetracycline hydroxchoride, Rolitetracycline, Doxycycline hydrochloride, Ampicillin, Piperacillin, Ticarcillin, Cefalotin, Cefaloridine, Cefotiam, Cefsulodin, Cefmenoxime, Cefmetazole, Cefazolin, Cefotaxime, Cefoperazone, Ceftizoxime, Moxalactam, Thienamycin, Sulfazecin, Azthreonam, Cefotiam hexetil hydrochloride, acetoxymethyl (+)-(5R, 6S)-6-[(R)-1-hydroxyethyl]-7-oxo-3-(3-pyridyl)-4-thia-1-azabicyclo[3.2.0]hept-2-ene-2-carboxylate and the like.

Examples of antipyretics, analgesics and anti-inflammatory agents include salicylic acid, sulpyrine, flufenamic acid, diclofenac, indomethacin, morphine, pethidine hydrochloride, levorphanol tartrate, oxymorphone and the like.

Examples of antitussive expectorants include ephedrine hydrochloride, methylephedrine hydrochloride, noscapine hydrochloride, codeine phosphate, dihydrocodeine phosphate, alloclamide hydrochloride, clofedanol hydrochloride, picoperidamine hydrochloride, cloperastine, protokylol hydrochloride, isoproterenol hydrochloride, salbutamol sulfate, terbutaline sulfate and the like.

Examples of bronchodilators include phenylpropanolamine hydrochloride, theophylline, salbutamol sulfate and the like.

Examples of sedativa include chlorpromazine, prochlorperazine, trifluoperazine, atropine sulfate, methylscopolamine bromide and the like.

Examples of muscle relaxants include pridinol methansulfonate, tubocurarine chloride, pancuronium bromide and the like.

Examples of antiepileptics include phenytoin, ethosuximide, acetazolamide sodium, chlordiazepoxide and the like.

Examples of antiulcer agents include benzimidazole compounds(U.S. Pat. Nos. 4,045,563, 4,255,431 and 4,472, 409; EP-A 45200, 5129, 174726, 175464 and 208452; GB-A 2134523), metoclopramide, histidine hydrochloride and the like.

Examples of antidepressant agents include imipramine, clomipramine, noxiptiline, phenelzine sulfate and the like.

Examples of antiallergic agents include diphenhydramine hydrochloride, chlorpheniramine maleate, tripelennamine hydrochloride, methdilazine hydrochloride, clemizole hydrochloride, diphenylpyraline hydrochloride, methoxyphenamine hydrochloride and the like.

Examples of cardiotonics include trans-π-oxocamphor, theophyllol, aminophylline, etilefrin hydrochloride and the like.

Examples of antiarrhythmic agents include propranolol, alprenolol, bufetolol, oxprenolol and the like.

Examples of vasodilators include oxyfedrine hydrochloride, diltiazem, tolazoline hydrochloride, hexobendine, bamethan sulfate and the like.

Examples of hypotensive diuretics include hexamethonium bromide, pentrinium, mecamylamine hydrochloride, ecarazine hydrochloride, clonidine and the like.

Examples of antidiabetics include insulin senstivity enhancer (EP-A 749751), voglibose, miglitol, glymidine sodium, glipizide, phenformin hydrochloride, buformin hydrochloride, metformin and the like.

Examples of antilipidemic agents include sodium 3R,5S-(+)-erythro-(E)-7-[4-(4-fluorophenyl)-2,6-diisopropyl-5-methoxymethyl-pyrid-3-yl]-3,5-dihydroxy-hept-6-enoate, pravastatin sodium, simvastatin, clinofibrate, clofibrate, simfibrate, bezafibrate and the like.

Examples of anticoagulants include heparin sodium and the like.

Examples of hemostatics include thromboplastin, thrombin, menadion sodium bisulfite, acetomenaphtone, ε-aminocaproic acid, tranexamic acid, carbazochrome sodium sulfonate, adrenochrome monoaminoguanidine methanesulfonate and the like.

Examples of antituberculous agents include isoniazid, ethambutol, para-aminosalicylic acid and the like.

Examples of hormones include prednisolone, prednisolone sodium phosphate, dexamethasone sodium sulfate, betamethasone sodium phosphate, hexoestrol phosphate, hexoestrol acetate, methimazole and the like.

Examples of narcotic antagonists include levallorphan tartrate, nalorphine hydrochloride, naloxone hydrochloride and the like.

Examples of bone resorption inhibitory agents include ipriflavone and the like.

Examples of osteogenesis promoting agents include polypeptides such as BMP, PTH, TGF-β, IGF-1 and the like, (2R,4S)-(−)-N-[4-(diethoxyphosphorylmethyl)phenyl]-1,2, 4,5-tetrahydro-4-methyl-7,8-methylenedioxy-5-oxo-3-benzothiepine-2-carboxamide, 2-(3-piridyl)-ethane-1,1-diphosphonic acid and the like.

Examples of angiogenesis inhibitory agents include angiogenesis inhibitory steroids [Science, 221, 719 (1983)], fumagillin (EP-A 325199), fumagillol derivatives (EP-A 357061, 359036, 386667 and 415294) and the like.

Examples of vitamins include cyanocobalamine, thiamine, ascorbic acid, pantothenic acid and the like.

The above-described pharmacologically active components may be in the form of pharmaceutically acceptable salts. Examples of such salts include salts with inorganic acids (e.g., hydrochloric acid, sulfuric acid, nitric acid, etc.), organic acids (e.g., carbonic acid, bicarbonic acid, succinic acid, acetic acid, propionic acid, trifluoroacetic acid, etc.), inorganic bases (e.g., alkali metals such as sodium, potassium, etc. and alkaline earth metals such as calcium, magnesium, etc.) and organic bases (organic amines such as triethylamine, etc. and basic amino acids such as arginine, etc.).

Among the above-described pharmacologically active components, those having high moisture-sensitivity are apt to show changes in their properties during the production of pharmaceutical preparations by conventional pharmaceutical technique and are difficult to handle. The present invention is applicable to even such high moisture-sensitive components and provides a novel method for producing pharmaceutical preparations of such high moisture-sensitive pharmacologically active components.

The term "high moisture-sensitive component" means a component which undergoes chemical changes (decomposition, coloring and the like) or physiological changes (change of crystalline form and the like) due to the presence of water.

The pharmacologically active components are preferably physiologically active peptides, antibiotics, bronchodilators, antilipidemic agents and vitamins. More preferably, the pharmacologically active component is antilipidemic agents, in particular, sodium 3R,5S-(+)-erythro-(E)-7-[ 4-(4-fluorophenyl)-2,6-diisopropyl-5-methoxymethyl-pyrid-3-yl]-3,5-dihydroxy-hept-6-enoate.

Examples of the sweeteners include starch sugar, reduced maltose, sorbitol, sucrose, fructose, lactose, honey, xylitol, saccharin, glycyrriza and its extracts, glycyrrhetic acid, hydrangea tea, aspartame and the like. Among them, aspartame which is a high moisture-sensitive component is preferred.

In addition to the above D-mannitol and components, the solid composition of the present invention may further contain any other excipients, disintegrators, binders, glidants, lubricants or the like, which are commonly employed for the preparation of food products or medicaments. Examples of such excipients include lactose, starch, sucrose, crystalline cellulose, anhydrous calcium hydrogenphosphate and calcium carbonate. Disintegrators are, for example, low-substituted hydroxypropylmethylcellulose, carboxymethylcellulose, carboxymethylcellulose calcium, carmellose, closcarmellose sodium, carboxymethyl starch sodium, partial pregeratinized starch and crospovidone. Binders are, for example, methylcellulose, hydroxypropylcellulose, hydroxypropyl methylcellulose, carboxymethylcellulose sodium, pregeratinized starch, acacia, agar, gelatine, tragacanth, sodium alginate, polyvinyl pyrrolidone and polyvinyl alcohol. Glidants are, for example, hydrated silicon dioxide, light anhydrous silicic acid, synthetic aluminum silicate, synthetic hydrotalcite, dried aluminum hydroxide gel, kaolin, calcium silicate and magnesium metasilicate aluminate. Lubricants are, for example, magnesium stearate, calcium stearate, stearic acid, talc, sodium lauryl sulfate, hydrogenated vegetable oil, microcrystalline wax, sucrose fatty acid ester and polyethylene glycol.

While the solid composition of the present invention can be produced by per se known technique, the D-mannitol of the present invention may be employed in the production step in a form prepared in advance, or may be added in the form of starting crystals to allow them to be transformed into the desired crystal shape during the production process of pharmaceutical preparations and food products.

Since the D-mannitol of the present invention, which has an increased binding points due to microcrystallization of the primary particles while retaining the inherent chemical and biological properties, has excellent compatibility and compressibility, it is remarkably useful as an excipient.

According to the method of the present invention, D-mannitol can be prepared conveniently and safely. Thus, the present invention contributes a great deal to the design of novel pharmaceutical preparations and food products and to the development of pharmaceutical manufacturing and food manufacturing techniques.

The following comparative examples and examples further illustrate the present invention, but they do not limit the scope of the present invention.

In the comparative examples and examples, the β form and δ form D-mannitol crystals were prepared by substantially the same manner as described in MICROSCOPE, 18, 279–285 (1970).

COMPARATIVE EXAMPLE 1

To 100 g of the β form D-mannitol crystals was added 20 g of purified water. The mixture was stirred in a mortar for 3 minutes to moisten the crystals evenly, which was subjected to vacuum drying (40° C., 16 hours), followed by pulverizing through a sieve of No. 16 mesh. The particles thus obtained (specific surface area: 0.5 $m^2$/g) were subjected to compression under the following conditions.

Compressing machine: Autograph (Shimadz Seisakusho Ltd.)
Compression rate: 10 mm/min.
Punch: 10 mmφ, flat
Weight: 400 mg

COMPARATIVE EXAMPLE 2

In a agitating granulator (Powrex, Vertical Granulator VG10 type), 1500 g of the β form D-mannitol crystals was evenly moistened with 375 g of purified water (200 rpm, 2 minutes), which was subjected to vacuum drying (40° C., 16 hours), followed by milling in a power mill (Showa Kagaku, P-3 type punching size: 1.5 mmφ). The powder thus obtained (specific surface area: 0.5 $m^2$/g; hereinafter called "β form crystals AG") was mixed as in the following formula and subjected to tabletting under the following conditions.

| Formula: | |
| --- | --- |
| β form crystals AG | 709.2 g |
| phenylpropanolamine hydrochloride | 78.8 g |
| magnesium stearate | 12.0 g |
| Total | 800.0 g |

Tabletting machine: Correct 19 AWC (Kikusui Seisakusho)
Tabletting pressure: 1200–2400 kg/$cm^2$
Rotational frequency: 30 rpm
Punch: 8.0 mmΦ, flat face beveled-edge
Weight: 180 mg

COMPARATIVE EXAMPLE 3

In a agitating granulator (Powrex, Vertical Granulator VG 10 type), a mixture of 1267.2 g of the β form D-mannitol crystals and 316.8 g of phenylpropanolamine hydrochloride was evenly moistened with 240 g of purified water (200 rpm, 2 minutes), which was subjected to vacuum drying (40° C., 16 hours), followed by milling in power mill (Showa Kagaku, P-3 type, punching size: 1.5 mmφ). A mixture of 792.0 g of thus-obtained powders and 8.0 g of magnesium stearate was subjected to tabletting under the following conditions.

Tabletting machine: Correct 19 AWC (Kikusui Seisakusho)
Tabletting pressure: 100–3000 kg/cm$^2$
Rotational frequency: 30 rpm
Punch: 8.0 mmφ, flat-face beveled-edge
Weight: 180 mg

COMPARATIVE EXAMPLE 4

In a agitating granulator (Powrex, Vertical Granulator VG 10 type), 1500 g of the β form D-mannitol crystals was evenly moistened with 375 g of purified water (200 rpm, 2 minutes), which was subjected to vacuum drying (40° C., 16 hours), followed by milling in power mill (showa Kagaku, P-3 type, punching size: 1.5 mmφ). The β form crystals AG (specific surface area: 0.5 m$^2$/g) was mixed as in the following formula and subjected to dry granulating. The slugs thus obtained were milled in power mill (Showa Kagaku, P-3 type, punching size: 2.0 mmφ).

| Formula: | |
| --- | --- |
| β form crystals AG | 709.2 g |
| phenylpropanolamine hydrochloride | 78.8 g |
| magnesium stearate | 12.0 g |
| Total | 800.0 g |
| Machine: Roller compactor (FREUND, Model-mini) | |
| Rotational frequency: 3 rpm | |
| Powder-feeding rate: 20 rpm | |
| Compression pressure: 50 kg/cm$^2$ | |
| Thickness of flakes: about 2.0 mm | |

EXAMPLE 1

To 100 g of the δ form D-mannitol crystals was added 20 g of purified water. The mixture was stirred in a mortar for 3 minutes to moisten the crystals evenly, which was subjected to vacuum drying (40° C., 16 hours), followed by pulverizing through a sieve of 16 mesh. The powders thus obtained (specific surface area: 1.9 m$^2$/g) were subjected to compression molding under the same conditions as in Comparative Example 1. On the other hand, as comparative compressed products, compressed products were prepared respectively using untreated δ form D-mannitol crystals (specific surface area: 0.7 m$^2$/g) and β form D-mannitol crystals (specific surface area: 0.5 m$^2$/g) in substantially the same manner. The hardness of the compressed product thus obtained and that of the compressed product in Comparative Example 1 were determined by an instrument of measuring tablet fracture strength (Toyama Sangyo). As the result, no difference of hardness was recognized, under the above-described compression conditions, among the three compressed products using untreated δ form crystals, untreated β form crystals and treated β form crystals (Comparative Example 1). The hardness of the compressed product prepared in this Example 1 was found to be remarkably high as compared with the compressed product prepared by using untreated δ form crystals or treated β form crystals (FIG. 1).

Figure 2:
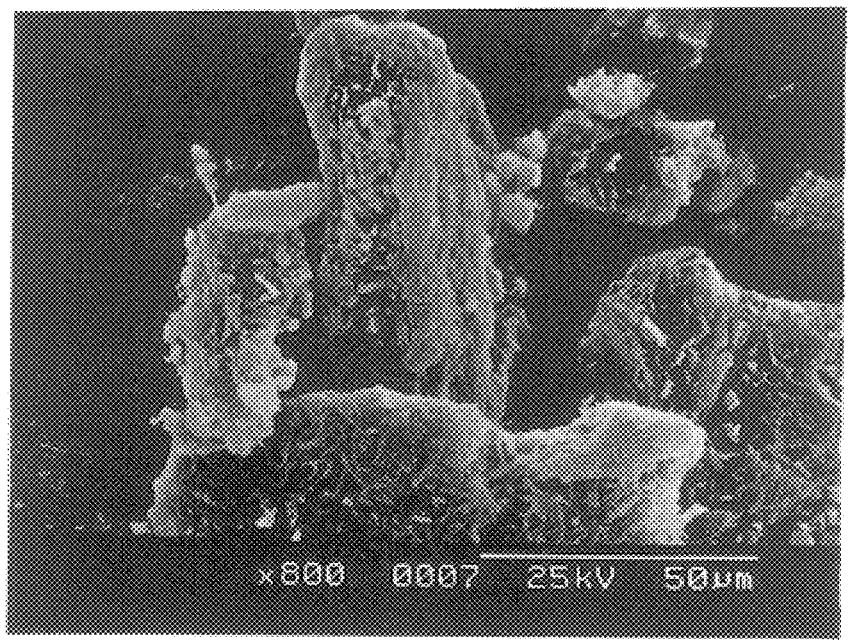
FIG. 2 is the scanning electron microscopic image of the D-mannitol of the present invention prepared in Example 1.
Figure 3:
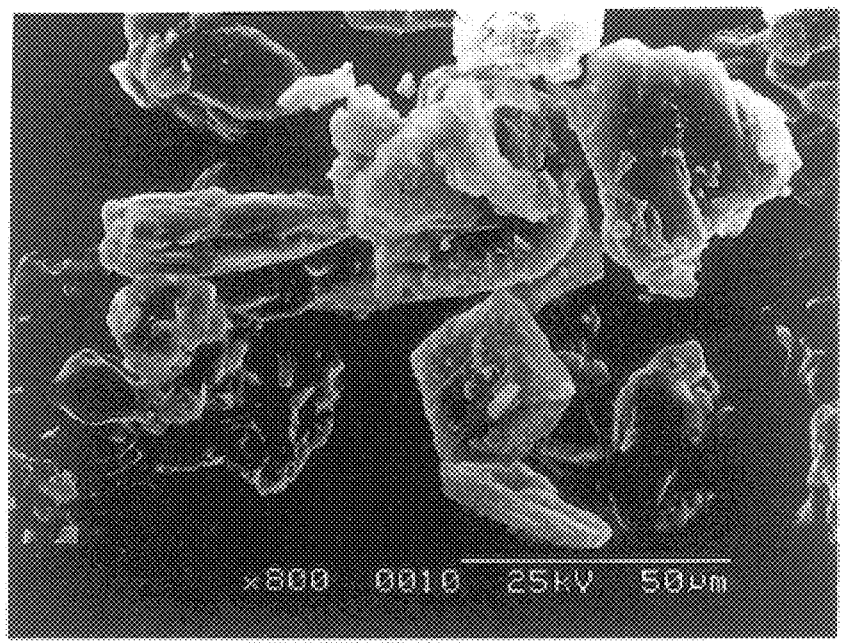
FIG. 3 is the scanning electron microscope image of the δ form crystals.
Figure 4:
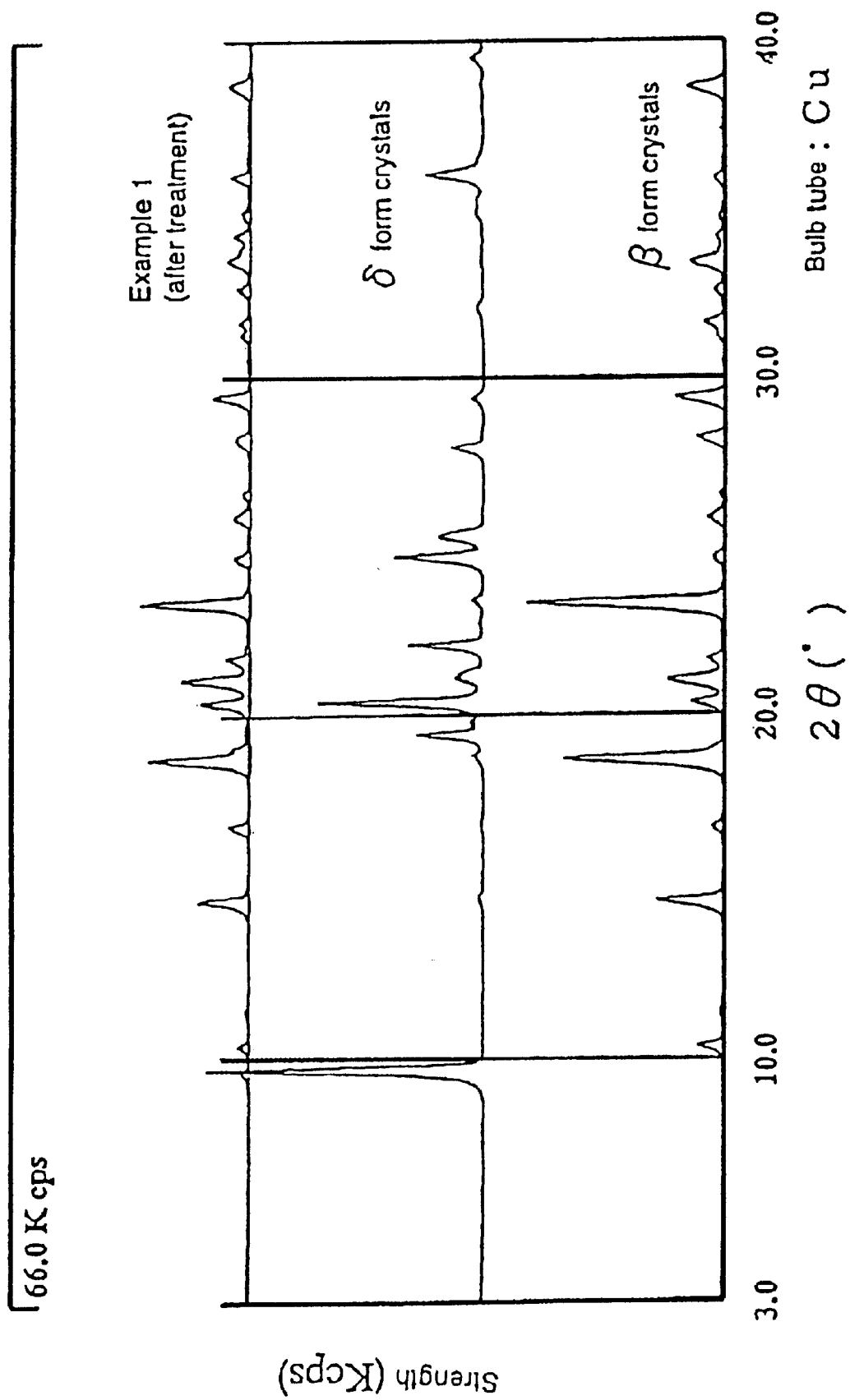
FIG. 4 is the respective powder X-ray diffraction patterns of the D-mannitol of the present invention and δ form and β form D-mannitol.

And, the D-mannitol of this Example 1 was, by observation under a scanning electron microscope, unlike the starting crystals (FIG. 3), porous particle consisting of fine-crystalline aggregates of D-mannitol (FIG. 2), whose powder X-ray diffraction spectrum was measured to confirm the transformation of δ form to β form (FIG. 4).

EXAMPLE 2

Figure 5:
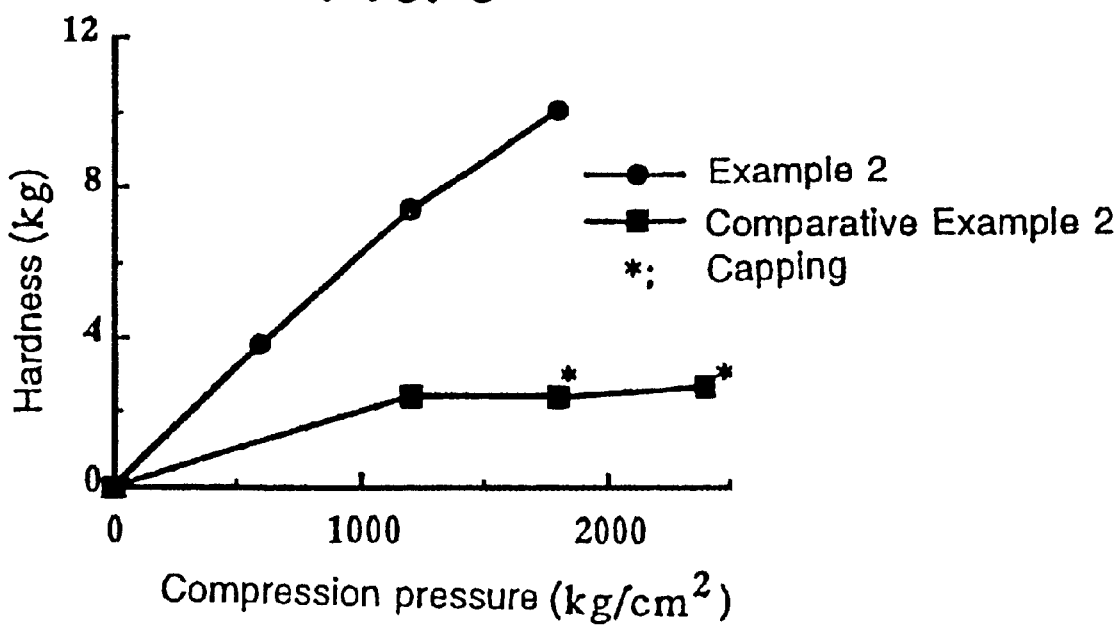
FIG. 5 is the respective hardness of the compressed product prepared in Example 2 and that of the compressed product prepared in Comparative Example 2 hereinafter.

In a agitating granulator (Powrex, Vertical Granulator VG10 type), 1500 g of the δ form D-mannitol crystals was evenly moistened with 375 g of purified water (200 rpm, 2 minutes), which was subjected to vacuum drying (40° C., 16 hours), followed by milling in power mill (Showa Kagaku, P-3 type punching size: 1.5 mmφ). The powder thus obtained (specific surface area: 1.9 m$^2$/g; hereinafter called "δ form crystals AG") was mixed as in the following formula and subjected to tabletting. The hardness of the compressed product thus obtained and that of the compressed product of the Comparative Example 2 were determined by an instrument of measuring tablet fracture strength (Toyama Sangyo). The results showed that the compressed product of this Example 2 showed remarkably excellent compressibility and gave sufficient hardness with a low tabletting pressure, while the compressed product of Comparative Example 2 showed poor compressibility and capping occurred with a tabletting pressure of 1800 kg/cm$^2$ or more to give no satisfactory tablets (FIG. 5).

| Formula: | |
| --- | --- |
| δ form crystals AG | 709.2 g |
| phenylpropanolamine hydrochloride | 78.8 g |
| Magnesium stearate | 12.0 g |
| Total | 800.0 g |
| Tabletting machine: Correct 19 AWC (Kikusui Seisakusho) | |
| Tabletting pressure: 600–1800 kg/cm$^2$ | |
| Rotational frequency: 30 rpm | |
| Punch: 8.0 mmΦ, flat-face beveled-edge | |
| Weight: 180 mg | |

EXAMPLE 3

Figure 6:
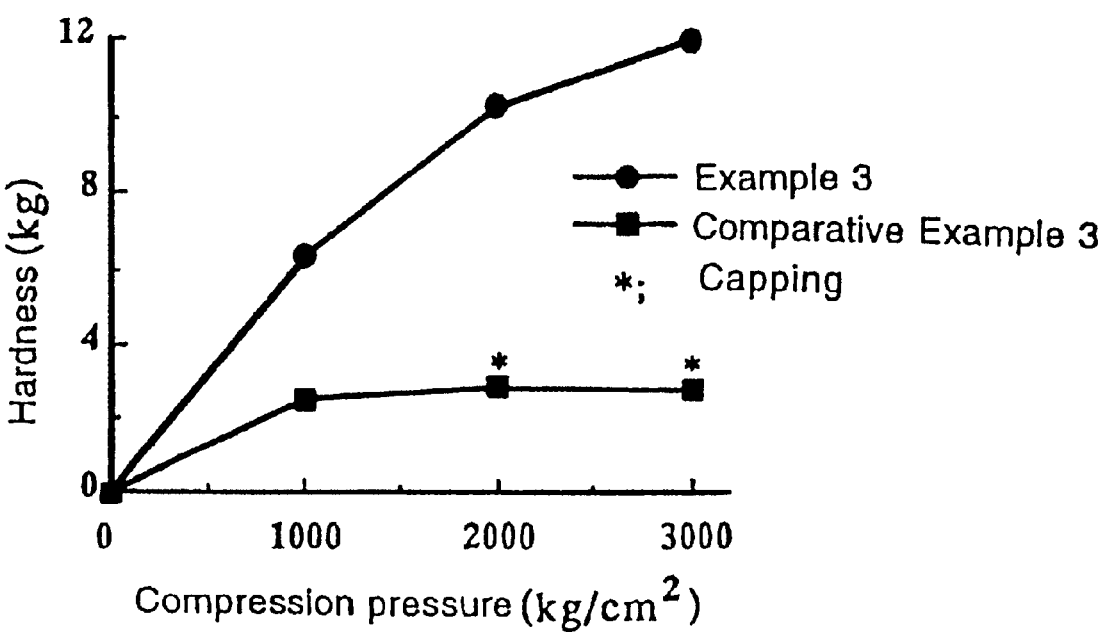
FIG. 6 is a graph illustrating the respective hardness of the compressed product in Example 3 and that of the compressed product of Comparative Example 3 hereinafter.

In an agitating granulator (Powrex, Vertical Granulator VG 10 type), a mixture of 1267.2 g of the δ form D-mannitol crystals and 316.8 g of phenylpropanolamine hydrochloride was evenly moistened with 240 g of purified water (200 rpm, 2 minutes), which was subjected to vacuum drying (40° C., 16 hours), followed by milling in power mill (Showa Kagaku, P-3 type, punching size: 1.5 mmφ). A mixture of 792.0 g of thus-obtained powders and 8.0 g of magnesium stearate was subjected to tabletting under the following conditions. The hardness of the compressed product was determined by an instrument of measuring tablet fracture strength (Toyama Sangyo). As a result, the compressed product of this Example 3 showed remarkably excellent compressibility and gave sufficient hardness, while the compressed product of Comparative Example 3 which was prepared by using β form D-mannitol crystals showed poor compressibility and capping was occurred with a tabletting pressure of 2000 kg/cm$^2$ or more to give no satisfactory tablets (FIG. 6).

Tabletting machine: Correct 19 AWC (Kikusui Seisakusho)
Tabletting Pressure: 1000–3000 kg/cm$^2$
Rotational frequency: 30 rpm Punch: 8.0 mmφ, flat-face beveled-edge
Weight: 180 mg

EXAMPLE 4

Figure 7:
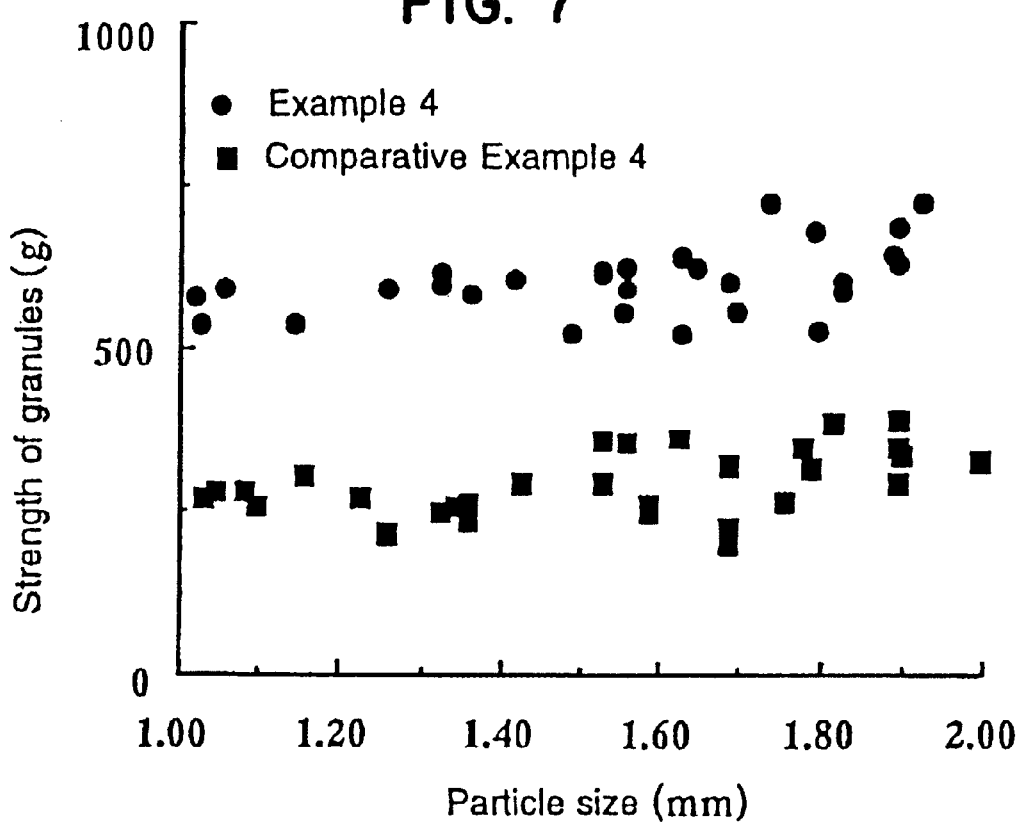
FIG. 7 is a graph illustrating the respective strength of the compressed product of Example 4 and that of the compressed product of Comparative Example 4.

In an agitating granulator (Powrex, Vertical Granulator VG 10 type), 1500 g of the δ form D-mannitol crystals was evenly moistened with 375 g of purified water (200 rpm, 2 minutes), which was subjected to vacuum drying (40° C., 16 hours), followed by milling in power mill (Showa Kagaku, P-3 type, punching size: 1.5 mmφ). The δ form crystals AG thus obtained (specific surface area: 1.9 m$^2$/g) was mixed as in the following formula and subjecting to dry granulating under the same conditions as in Comparative Example 4. The slugs thus obtained were milled in power mill (Showa Kagaku, P-3 type, punching size: 2.0 mmφ). The strength of the granules was determined by an instrument measuring granular length (Okada Seiko, Grano), and the results were shown in (FIG. 7), from which the average granular strength of the both products was calculated (n=30; 1.0–2.0 mm) to find that the average granular strength of the granules of this Example 4 was 601.7 g, while that of the granules of Comparative Example 4 was 292.0 g.

As is clear from the results, the formula in this Example 4 using the δ form crystals AG gave hard granules containing little micropowders and showed excellent properties for filling in capsules. On the other hands, since the strength of the granules obtained by the formula in Comparative Example 4 using β form crystals AG was not sufficient, encapsulation of them was difficult.

Formula:

| | |
|---|---|
| δ form crystals AG | 709.2 g |
| phenylpropanolamine hydrochloride | 78.8 g |
| magnesium stearate | 12.0 g |
| Total | 800.0 g |

EXAMPLE 5

Figure 8:
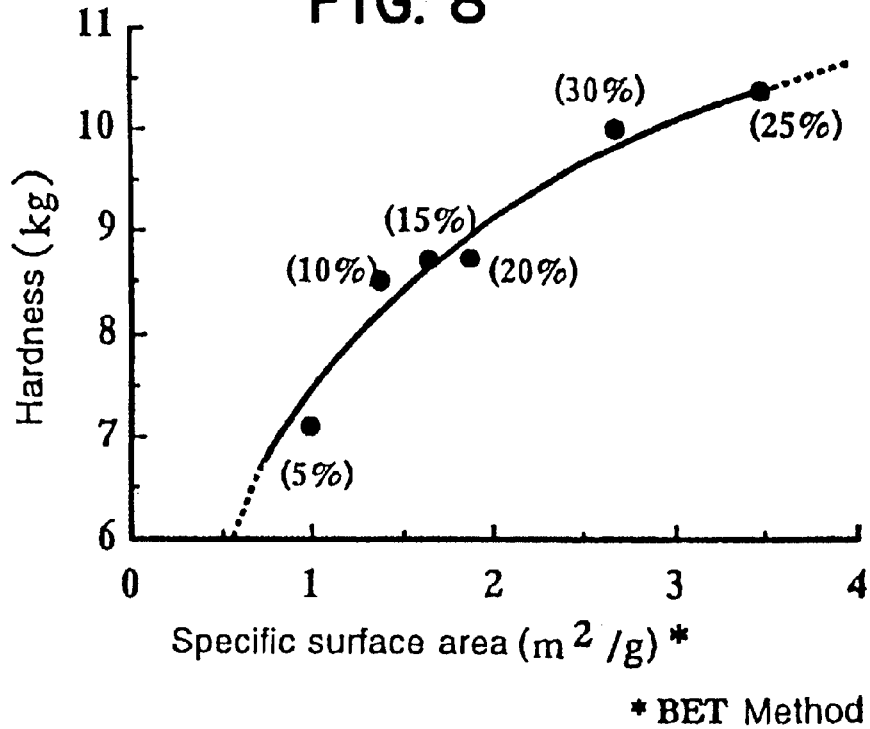
FIG. 8 is a graph illustrating the relation of the amount of purified water used for treatment of the δ form crystals with the properties of the resultant D-mannitol.

To agitating granulators (Powrex, Vertical Granulator VG 10 type) each containing 1000 g of δ form D-mannitol crystals, 50, 100, 150, 200, 250 and 300 g of purified water (5–30 w/w% based on the weight of mannitol) were respectively added en bloc. The respective mixtures were agitated (2 minutes, 200 rpm), followed by vacuum drying (40° C., 16 hours). Each dried material was milled in power mill (Showa Kagaku, P-3 type, punching size: 1.5 mmφ). The thus obtained powder (specific surface areas: 1.0, 1.4, 1.7, 1.9, 3.5 and 2.7 m$^2$/g, respectively) was subjected to tabletting under the following conditions. The hardness of the compressed product was determined by an instrument of measuring tablet fracture strength (Toyama Sangyo). The specific surface area of the powders was measured by BET method. The results showed that the volume of water used for the treatment gave an influence on the specific surface area of the product obtained by treatment of the crystals to correspondingly influence on the hardness of the compressed product (FIG. 8). In FIG. 8, numerical values in the parentheses show % by weight of the purified water used relative to the weight of δ form D-mannitol crystals.

Tabletting machine: Correct 19 AWC (Kikusui Seisakusho)
Tabletting pressure: 2000 kg/cm$^2$
Rotational frequency: 30 rpm
Punch: 8.0 mmΦ, flat-face beveled-edge
Weight: 180 mg

EXAMPLE 6

5.043 kg of δ form D-mannitol was treated in a high shear mixer (Loedige MGT-30) with a granulation liquid comprising of 6 g of sodium 3R,5S-(+)-erythro-(E)-7-[4-(4-fluorophenyl)-2,6-diisopropyl-5-methoxymethyl-pyrid-3-yl]-3,5-dihydroxy-hept-6-enoate (cerivastatin), 108 g of polyvinyl pyrrolidone (polyvidone 25) and 420 g of purified water. The wet granulation mass was rasped and then dried in a fluidized bed dryer (inlet air temperature 60–80° C.) until a residual moisture content of preferably 1.5% or less was reached. The granules were sieved (oscillation sieve, 0.8 mm) and then blended with 162 g of crospovidone and 81 g of magnesium stearate. Compression of the granulates under the following conditions resulted in tablets with favorable hardness.

Tabletting machine: Kilian T 200
Compression force: 6–8 kN
Punch size:

6 mm diameter
9 mm radius of curvature
Tablet weight: 90 mg

What is claimed is:

1. A solid composition comprising a pharmacologically active component and D-Mannitol, said D-Mannitol (a) being in the β form crystals alone or a mixture of the β form crystals with the δ form crystals, (b) having a specific surface area of not less than about 1 m$^2$/g and (c) being produced by a process which comprises moistening the surface of δ form D-Mannitol crystals with a water-soluble solvent without dissolving the δ form D-Mannitol crystals completely in the water-soluble solvent, followed by drying the moistened δ form D-Mannitol crystals to obtain the D-Mannitol.

2. The solid composition according to claim 1 wherein the pharmacologically active component is a highly moisture-sensitive component.

3. The solid composition according to claim 1, wherein the pharmacologically active component is selected from the group consisting of physiologically active peptides, antitumor agents, antibiotics, antipyretics, analgesics, anti-inflammatory agents, antitussive expectorants, bronchodilators, sedativa, muscle relaxants, antiepileptics, antiulcer agents, antidepressant agents, antiallergic agents, cardiotonics, antiarrhythmic agents, vasodilators, hypotensive diuretics, antidiabetics, antilipidemic agents, anticoagulants, hemostatics, antituberculous agents, hormones, narcotic antagonists, bone resorption inhibitory agents, osteogenesis promoting agents, angiogenesis inhibitory agents and vitamins.

\* \* \* \* \*

UNITED STATES PATENT AND TRADEMARK OFFICE
CERTIFICATE OF CORRECTION

PATENT NO.     : 6,503,918 B2
DATED          : January 7, 2003
INVENTOR(S)    : Tomohiro Yoshinari et al.

It is certified that error appears in the above-identified patent and that said Letters Patent is hereby corrected as shown below:

<u>Title page,</u>
Item [60], please amend the following section:
-- [60] Continuation of application No. 09/650,722, filed on Aug. 30, 2000, now abandoned, which is a divisional of application No. 09/155,978, filed on Oct. 23, 1998, now Patent No. 6,235,947, which is a §371 of PCT/JP97/01286 filed April 14, 1997. --

Signed and Sealed this

Twenty-fifth Day of November, 2003

JAMES E. ROGAN
*Director of the United States Patent and Trademark Office*